US005614010A

United States Patent [19]

Smith et al.

[11] Patent Number: 5,614,010
[45] Date of Patent: Mar. 25, 1997

[54] HYDROCARBON GELS USEFUL IN FORMATION FRACTURING

[75] Inventors: Kevin W. Smith, McMurray; Leonard J. Persinski, Pittsburgh, both of Pa.

[73] Assignee: Clearwater, Inc., Pittsburgh, Pa.

[21] Appl. No.: 592,592

[22] Filed: Jan. 26, 1996

Related U.S. Application Data

[60] Continuation-in-part of Ser. No. 360,438, Dec. 21, 1994, abandoned, which is a division of Ser. No. 209,266, Mar. 14, 1994, Pat. No. 5,417,287.

[51] Int. Cl.$^6$ ....................................................... E21B 43/26
[52] U.S. Cl. ...................................... 106/285; 106/287.18
[58] Field of Search ................................ 106/285, 287.18

[56] References Cited

U.S. PATENT DOCUMENTS

| | | | |
|---|---|---|---|
| 3,338,935 | 8/1967 | Kerschner et al. | 260/429.5 |
| 3,575,859 | 4/1971 | Monroe | 252/32.5 |
| 5,271,464 | 12/1993 | McCabe | 166/295 |

Primary Examiner—David Brunsman
Attorney, Agent, or Firm—William L. Krayer

[57] ABSTRACT

This invention relates to improved hydrocarbon gels finding use in the fracturing of formations which produce petroleum and other hydrocarbons. The gelling agents comprise combinations of ferric salts, selected orthophosphate esters, a low molecular weight amine such as triethonolamine or triethylamine, and a surfactant.

16 Claims, No Drawings

HYDROCARBON GELS USEFUL IN FORMATION FRACTURING

RELATED APPLICATIONS

This application is a continuation-in-part of our application Ser. No. 08/360,438 of the same title filed Dec. 21, 1994, now abandoned, which is a division of our application Ser. No. 08/209,266, also of the same title, filed Mar. 14, 1994, now U.S. Pat. No. 5,417,287.

TECHNICAL FIELD

This invention relates to improved hydrocarbon gels which find use in petroleum producing formation fracturing. In particular it relates to the use of a defined class of gelling agents for hydrocarbons which provide excellent results in such fracturing.

The gelling agents are combinations of ferric salts; low molecular weight amines, and selected orthophosphate esters with or without optional surfactants.

BACKGROUND OF THE INVENTION

The development of the use of gelled hydrocarbons as fracturing fluids is reviewed by Weldon M. Harms in a chapter entitled "Application of Chemistry in Oil and Gas Well Fracturing", at pages 59–60 of the book "Oil-Field Chemistry (ACS Symposium #396–1988)" published by the American Chemical Society in 1989. The basic technique of formation fracturing involves the injection of a fracturing fluid down the well bore, which is usually cemented in place and at least 0.3 mile long, and then through horizontal holes in the steel pipe, or casing, of the well, to obtain access to the subterranean formation. The fracturing fluid is under high pressure and must be able to survive the severe shear forces caused when flow is forced through the casing perforations of perhaps ¼ to ½ inch in diameter, as well as the shear forces encountered at the leading edge of the fracture. Whatever chemical additives are used to influence viscosity, induce gel formation, stabilize against resident chemicals, pH or temperature conditions in the formation, inhibit scale formation or corrosion, or inhibit paraffin deposition, for example, must also be able to withstand the shear forces and other inhospitable conditions of use. Most commonly available liquids typically are viscosified before they are particularly effective in carrying the large quantities of proppants widely used in the fracturing process.

When hydrocarbons are used in the fracturing process, they are commonly treated to increase their viscosity. As reviewed by Harms, an early viscosifying agent was napalm, an aluminum soap of fatty acids. Aluminum salts of orthophosphate esters were introduced in the late 1960's, followed by the suggestion of the use of $Fe_3O_4$ for combination with the orthophosphate esters, in Monroe U.S. Pat. No. 3,505,374. While many other combinations of metals and other materials have been suggested as viscosifying agents, aluminum crosslinked orthophosphate esters are still, according to Harms, the most widely used.

The aluminum compounds present problems, however, particularly where any significant amount of water is present. They generally will not satisfactorily perform the desired crosslinking function in the presence of more than about 1200 ppm of water, nor where the pH is outside a relatively narrow range. Moreover, an inadvertent excess of aluminum compound treatment is detrimental to the desired performance because the aluminum compound itself adversely affects the pH. The iron provided by ferric salts as in the present invention, on the contrary, permits operation in wider pH ranges.

In describing a gel which can be used as a pig in a pipeline, Jaggard et al in U.S. Pat. No. 4,003,393 recite the possibility of iron as one of a number of metals to combine with a class of aliphatic substituted orthophosphoric esters. No other qualifiers are used to describe the iron, however.

In U.S. Pat. No. 4,153,649, Griffin proposes reacting a pentavalent phosphorous compound with a class of hydroxy ethers before employing the metal salt. Among the metal salts he uses is ferric nitrate, but he further requires a "separate source of base" to be used with the hydroxy ether modified phosphates, as spelled out in column 4, lines 55–58 and column 11, lines 37–68.

Monroe, in U.S. Pat. No. 3,505,374, uses a gelling agent for hydrocarbons characterized as a ferroso-ferric salt of an alkyl oleyl diester of orthophosphoric mono acid. The iron compound is further described as magnetite, or $Fe_3O_4$. He suggests this combination for fracturing subterranean oil-bearing formations, but says none of the "other oxidized forms of iron including ferrous and ferric oxides and hydroxides, chlorides, sulfates and nitrates" (col 3, lines 2–4) yielded a gel as obtained with the magnetite.

Burnham, in U.S. Pat. No. 4,200,540, describes a large class of phosphates and phosphate esters which he mixes with aluminum salts, aluminates and aluminum metal. He chooses combinations of the materials as a function of various down-hole temperatures. No mention is made of iron salts; the reference is cited mainly for its comprehensive description of the phosphates deemed to be useful. See also Burnham's U.S. Pat. No. 4,316,810.

SUMMARY OF THE INVENTION

We have found that ferric salts can be very advantageously used in the gelling of hydrocarbons, particularly for use in formation fracturing, rather than aluminum compounds, for combination with orthophosphate esters.

The ferric salt has the advantage that it can be used in the presence of large amounts of water, such as up to 20%. One of the advantages of fracturing with hydrocarbon gels is that some formations may tend to imbibe large quantities of water, while others are water-sensitive and will swell inordinately if water is introduced; our invention permits one to use a hydrocarbon gel in areas where water may cause trouble not only with the formation itself, but with the fracturing agent or the gelling agent. Also, it is not adversely affected by commonly used alcohols, such as methanol and isopropanol. In addition, it can be used in broad ranges of pH, yet the linkages it forms can still be broken with gel breaking additives conventionally used for that purpose. In addition, ferric salts such as ferric sulfate crosslink rapidly and can be made to link even more rapidly with the use of surfactants and/or alkaline or caustic agents such as potassium hydroxide. This continuation-in-part application is directed specifically to combinations of the ferric salts, particularly ferric sulfate, with low molecular weight amines such as triethylamine and triethanolamine, referred to herein sometimes interchangeably as TEA. Other low molecular weight amines useful in our invention are within the generic description found elsewhere herein and include monoisopropanol, butyl amine, and hexyl amine.

When dissolved in a hydrocarbon such as gasoline, diesel oil, crude oil, or kerosene, the ferric salt in combination with orthophosphate esters as defined below will cause the hydrocarbon to gel. The gel is generally stable to heat, and the degree of gelling can be controlled by the concentration of orthophosphate ester in the fluid.

DETAILED DESCRIPTION OF THE INVENTION

The phosphate ester which we use is advantageously added first and mixed with the Diesel fuel or other hydrocarbon to be used as the fracturing agent, generally in amounts from about 0.3% to about 1.5% by weight, based on the total. Then the ferric salt is added in amounts to provide preferably about one mole of ferric iron for each mole of phosphate or phosphate ester. In this manner, the process materials can be prepared more or less continuously, as opposed to the batch approach sometimes used in the past. More broadly we may use any amount of ferric salt which is effective to make a gel with the phosphate ester. This will be accomplished at about 0.1 to about 1.5 mole of ferric iron for each mole of phosphate ester, preferably 0.8:1 to 1.2:1.

A low molecular weight amine is also employed. The low molecular weight amine is preferably one of the formula $N(CH_2CH_2R)_3$ where R is H or OH, but may be any amine of the formula $H_{3-n}N(CH_mH_{2m}R)_n$ where m is an integer from 2–6, and n is an integer from 1–3, the alkylene group represented by $C_mH_{2m}$ may be linear or branched. Further examples of such compounds are diisopropylamine, triisobutylamine, and pentylamine.

The low molecular weight amine is advantageously first mixed with the ferric salt in a molar ratio of ferric salt to amine of about 0.25:1 to about 6:1. This is accomplished by thorough blending.

We have also found that surfactants have the effect of decreasing the time for crosslinking. Generally, in the absence of a surfactant, our combination of materials will crosslink in about two minutes at room temperature; when a surfactant is used also, this time is significantly reduced, and in the presence of our preferred class of surfactants, it is reduced to the neighborhood of twenty seconds, as determined by viscosity tests. About 0.1% to about 10% (based on the gelling agent) of surfactant is frequently advantageous also.

The phosphate derivatives we use are described in the literature as orthophosphate esters. They are similar to those used by Burnham in U.S. Pat. Nos. 4,200,540 and 4,316,810, Griffin in U.S. Pat. Nos. 4,174,283 and 4,153,649, and Harris et al in U.S. Pat. No. 4,622,155, having the structural formula

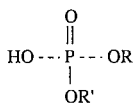

where R is a straight or branched chain alkyl, aryl, alkoxy, or alkaryl group having about 6 to about 18 carbon atoms and R' is hydrogen or an aryl, alkaryl, alkoxy, or alkyl group having up to about 18 carbon atoms. This structural formula will be referred to elsewhere herein as $HPO_4RR'$.

In the fracturing fluid, the iron from the ferric sulfate or other ferric salt forms linkages with the available oxygen, generally in more than one phosphate group, thus forming small chains which cause the hydrocarbon to gel.

It has been demonstrated in the laboratory that our invention may be used to form hydrocarbon gels, and that the gels can be broken in a manner familiar to persons who work with hydrocarbon gels in the field such as by the addition of common alkaline materials. In the following examples, and in the results reported in Tables I–IV, the procedure was to employ a laboratory Waring blender with a voltage regulator set at 25. 300 ml of Diesel oil was placed in the blender and the power turned on. The phosphate ester preparation was first added and after it was blended, the ferric salt solution was introduced by pipette. The time was recorded from the initial introduction of the ferric compound to the gel point, determined by a concave shape of the material in the blender. Blending was continued to determine the time required to reach maximum gel, which was estimated to be the first sign of conversion of the shape of the material to convex instead of concave. The blending was then stopped and the material transferred to a sample container, observing the consistency of the gel. Brookfield viscosity readings were then taken as shown in the Table I.

In the examples below, Composition M is about two-thirds phosphate ester of the above formula $HPO_4RR'$, together with 10% triethanolamine, and solvent. Composition L contains about two-thirds phosphate ester $HPO_4RR'$, together with 10% triethylamine, and high flash aliphatic solvent. Composition K is two-thirds of the same phosphate ester and 15.5 g 45%KOH, also with a solvent. Composition F contains about 27% ferric sulfate, together with ethylene glycol, mixed surfactants, 10% triethanolamine, and water. In each case, the amounts of composition M shown were added first to the Diesel oil and blended; then the amount shown of Composition F was added and blended. Results are presented in Table I.

TABLE I

| Ex | M | F | X-link | Invers | Spindl | 5 min | 30 min | 60 min |
|---|---|---|---|---|---|---|---|---|
| 1 | 3 ml | 3 ml | 20 sec | 30 sec | #3 | 2500 | — | 3890 |
| 2 | 3 ml | 3 ml | 20 sec | 30 sec | #3 | 2300 | — | 3460 |
| 3 | 3 ml | 3 ml | 25 sec | 35 sec | #3 | 2375 | — | 3400 |
| 4 | 3 ml | 3 ml | 30 sec | 60 sec | #4 | 6360 | 11000 | 13800 |
| 5 | 3 ml | 3 ml | 30 sec | 55 sec | #4 | 7320 | 12300 | 13500 |
| 6 | 3 ml | 3 ml | 45 sec | none at 180 sec | | | | |
| 7 | 2 ml | 2 ml | 60 sec | 150 sec | #4 | — | — | — |
| 8 | 3 ml* | 3 ml | 20 sec | 55 sec | #3 | 10000& | — | 13000& |

TABLE I-continued

| Ex | M | F | X-link | Invers | Spindl | 5 min | 30 min | 60 min |
|----|---|---|--------|--------|--------|-------|--------|--------|
| 9  | 6 ml* | 3 ml | 15 sec | 30 sec | #4 | — | — | 21500& |
| 10 | 2 ml$ | 3 ml | 20 sec | 35 sec | #4 | 13650& | — | 13850& |

*Composition L used instead of M
$Composition K used instead of M
&rotation at 10 rpm Persons skilled in the art will recognize from Table I that the formulations make excellent gels.

In a separate experiment, it was shown that the order of addition of the phosphate ester solution (sometimes herein called the gellant) and the ferric sulfate component (activator) is not important. In this experiment, 6.16 g deionized water and 1.3 g ferric sulfate were added to 85.95 g Diesel oil and mixed with the blender; then 0.4 ml of phosphate esters of the formula $HPO_4RR'$ was added and inversion took place in about one minute.

The data in Table II demonstrate that our hydrocarbon gel former will operate in the presence of significant amounts of water; indeed the viscosity increases with increasing amounts of water. In this experiment, an initial mixture was made as above with 4 g of gellant and 10 g of activator in about 250 g of Diesel oil. Water was then added incrementally and the viscosity measured immediately.

TABLE II

| Cumulative Water, % | Viscosity ($511\ sec^{-1}$) |
|---|---|
| 0.65% | 1 cp |
| 1.27% | 6 cp |
| 2.16% | 12 cp |
| 2.78% | 19 cp |
| 3.50% | 26 cp |
| 4.18% | 29 cp |
| 5.06% | 30 cp |
| 6.17% | * |
| 7.58% | * |
| 8.38% | * |
| 10.41% | * |
| 14.78% | * |
| 20.2% | * |

* Dial bouncing and unreadable; excellent lipping gel observed.

Additional tests were made as shown in Table III, which records the viscosities achieved by various combinations within our invention.

TABLE III

| ml M | ml F | cps | ml other comment |
|------|------|-----|------------------|
| 3 | 3 | 13,800 | |
| 3 | 3 | 13,500 | |
| 2 | 2 | (bouncing dial) | |
| a | 3 | 13,000 | |
| b | 3 | 21,500 | 6 TEA* |
| c | 3 | 13,900 | 2 KOH |
| 3 | 3 | 15,000 | |
| 3 | 3 | 16,000 | |
| d | 3 | 5,800 | low acid value PE |
| e | 3 | 9,400 | high acid value PE |
| f | 3 | 20,800 | KOH |
| g | 3 | 11,300 | ½ KOH |
| 3 | 3 | 7,000 | ¾ KOH |
| 3 | 3 | 8,600 | no TEA in F |
| 3 | 3 | 8,700 | KOH in M; no TEA in F |
| 3 | 3 | 14,500 | KOH in M; no TEA |
| 3 | 3 | 13,400 | |
| 3 | 3 | — | 4400 cps @ 20 rpm |
| i | 3 | 9,300 | |
| j | 3 | 20,400 | |
| 2 ml | 3 | 12,700 | |
| 2 ml | 1.5 | 8,300 | |
| k | 1.5 | 10,000 | |
| l | 1.5 | 12,500 | 2 ph est; KOH; 1.5 Fe |
| 3 | 3 | 14,700 | |
| m | 3 | 20,000 | |
| 3 | 3 | 23,000 | 0.25 g $Na_2CO_3$ |
| n | 3 | 21,000 | |
| o | 3 | 18,400 | 0.25 g $NA_2CO_3$ |
| 3 | 3 | 19,500 | 0.5 g $CaCl_2$ |
| p | 3 | 13,800 | 0.5 g $CaCl_2$ |
| 2 | 3 | 7,000 | |
| q | 3 | 11,600 | |
| r | 3 | 12,100 | |
| 3 | 3 | 10,500 | |
| 3 | 3 | 10,500 | Fe Citrate |
| 3 | 3 | 9,700 | |
| 3 | 3 | 6,800 | Fe Citrate |
| u | 3 | 8,200 | |
| v | 3 | 18,400 | $Na_2CO_3$ |
| w | 3 | 21,000 | $Na_2CO_3$ |
| x | 3 | 10,000 | |
| y | 3 | 11,000 | |
| aa | 2 | 6,700 | |
| bb | 1 | 780 | |
| cc | 4 | 12,300 | |
| dd | 3 | 13,000 | |
| ee | 4 | 12,200 | |
| ff | 5 | 12,000 | |
| gg | 6 | 11,500 | |
| hh | 7 | 12,300 | |
| ii | 9 | 11,500 | |
| jj | 11 | 11,400 | |
| kk | 13 | 13,300 | |
| ll | 17 | 11,800 | |
| mm | 3 | 10,900 | |
| nn | 3 | 14,700 | |
| oo | 2 | 14,900 | |
| pp | 4 | 14,900 | |
| qq | 6 | 12,500 | |
| rr | 8 | 12,700 | |
| ss | 11 | 10,400 | |
| tt | 15 | 7,600 | |

In Table III, the following notes apply to the column headed "ml Other":

| | |
|---|---|
| a | triethylamine with phosphate ester of M - 3 ml |
| b | triethylamine with phosphate ester of M - 6 ml |
| c | KOH with phosphate ester of M - 2 ml |
| d | triethanolamine with varied phosphate ester - 3 ml |
| e | triethanolamine with varied phosphate ester - 3 ml |
| f | KOH with phosphate ester of M - 3 ml |
| g | same as f with half as much KOH - 3 ml |
| h | same as g with half as much KOH - 3 ml |
| i, m, n, o, p | KOH with phosphate ester of M - 3 ml |
| k, l | KOH with phosphate ester of M - 2 ml |

-continued

| | |
|---|---|
| q, r, s | KOH with varied phosphate ester - 2 ml |
| t, u, v, w, x, y | no alkali; phosphate ester of M - 3 ml |
| aa | 3 ml non-neut phosphate ester; 2 ml F |
| bb | 3 ml non-neut phosphate ester; 1 ml F |
| cc | 3 ml non-neut phosphate ester; 4 ml F |
| dd | 3 ml KOH-treated phosphate ester; 3 ml F |
| ee | 3 ml KOH-treated phosphate ester; 4 ml F |
| ff | 3 ml KOH-treated phosphate ester; 5 ml F |
| gg | 3 ml KOH-treated phosphate ester; 6 ml F |
| hh | 3 ml KOH-treated phosphate ester; 7 ml F |
| ii | 3 ml KOH-treated phosphate ester; 9 ml F |
| jj | 3 ml KOH-treated phosphate ester; 11 ml F |
| kk | 3 ml KOH-treated phosphate ester; 13 ml F |
| ll | 3 ml KOH-treated phosphate ester; 17 ml F |
| mm | 3 ml non-neut phosphate ester; 3 ml F |
| nn | 3 ml non-neut phosphate ester; 2 ml F |
| oo | 3 ml M; 4 ml F |
| pp | 3 ml M; 6 ml F |
| qq | 3 ml M; 8 ml F |
| rr | 3 ml M; 11 ml F |
| ss | 3 ml M; 15 ml F |
| * | 6 ml of triethanolamine instead of 3 ml |

From the above table III, it is apparent that a broad range of ferric salts, neutralizing agents, and other additives such as breakers, and other materials are not detrimental to the gelling abilities of our invention. In addition, it may be seen that triethanolamine and triethylamine are useful in concentrations of about one-half molar equivalent (3 ml in the above table) to about 1 molar equivalent (6 ml) with respect to the phosphate ester. We may use the low molecular weight amines in amounts from about one-fourth molar equivalent to about 1.5 molar equivalent or more.

In the following Table IV, ferric salts as shown were used in combination with a standard 3 ml concentration of phosphate ester solution, some with KOH and some without, in 300 ml oil. The viscosity was measured with a #4 spindle at 10 rpm unless otherwise noted.

TABLE IV

| Iron salt | ml Fe | Viscosity | Comment |
|---|---|---|---|
| Fe Citrate | 3 | 6,800 | |
| Fe Citrate | 1 | 8,800 | |
| Fe Citrate | 3 | 16,700 | |
| Fe Citrate | 3 | 7,000+ | |
| Fe Citrate | 2 | 8,000 | |
| Fe Citrate | 2.5 | 3,300 | #3 spndl; 10 rpm |
| Fe Citrate | 2.5 | 3,200 | " |
| Fe Citrate | 2.5 | 3,200 | " |
| Fe Citrate | 2.5 | 2,700 | " |
| Fe Amm Sulf | 1 | 13,000 | |
| Fe Amm Sulf | 1 | 3,500 | (20 rpm) |
| Fe Amm Sulf | 1.5 | 14,700 | |
| Fe Amm Sulf | 1.5 | 15,000 | |
| Fe Chloride | 3 | 6,200 | |
| Fe Chloride | 2 | 7,600 | |
| Fe Sulfate | 1 | 9,700 | |
| Fe Sulfate | 1.5 | 14,000 | |
| Fe Sulfate | 1 | 7,000 | |
| Fe Amm Citrate | 3 | 12,000 | |
| Fe Gluconate | 3 | 4,600 | |

Additional tests and demonstrations were made on combinations of ferric sulfate and low molecular weight amines. In the runs shown in Table V, Fann viscosity readings were taken on various gellant preparations including low molecular weight amines. For Table V, a solution (TC-23C) of 67% phosphate ester, 15% KOH and 18% solvent was prepared; this was mixed with a composition (TC-23E) comprising 54.4% ferric sulfate (40% solution) 15.9% triethanolamine, 18.7% ethylene glycol, 3% ammonium cumene sulfate, a surfacant (ACS) and 8% water. The shear rate in the Fann viscosimeter was maintained at 100±0.1. The temperature was elevated as shown in the table. The gel achieved a remarkably stable viscosity after about 30 minutes of shear.

TABLE V

| ELAPSED TIME Min. | SHEAR STRESS LB/100 $F^2$ | VISCOSITY (cP) | TEMP. °F. |
|---|---|---|---|
| 0 | 70.1 | 0 | 71 |
| 3 | 123.8 | 348 | 94 |
| 8 | 133.7 | 376 | 181 |
| 13 | 124.4 | 350 | 224 |
| 18 | 100.7 | 283 | 251 |
| 23 | 89.5 | 252 | 268 |
| 28 | 81.5 | 229 | 279 |
| 33 | 77.1 | 217 | 288 |
| 38 | 76.0 | 214 | 295 |
| 41 | 75.1 | 211 | 299 |
| 46 | 74.6 | 210 | 301 |
| 51 | 75.1 | 211 | 301 |
| 55 | 74.6 | 210 | 300 |
| 60 | 74.6 | 210 | 300 |
| 65 | 74.8 | 210 | 299 |
| 69 | 75.1 | 211 | 299 |
| 74 | 74.8 | 210 | 299 |
| 79 | 74.9 | 210 | 299 |
| 99 | 74.9 | 211 | 299 |

Table VI shows results using the same materials, in which the pressure was maintained at 240 psig (±2) throughout. The shear rate was 100±0.1 as in Table V.

TABLE VI

| ELAPSED TIME Min. | SHEAR STRESS LB/100 $F^2$ | VISCOSITY (cP) | TEMP. °F. |
|---|---|---|---|
| 0 | 77.1 | 0 | 109 |
| 4 | 120.6 | 339 | 144 |
| 9 | 126.9 | 357 | 168 |
| 14 | 138.1 | 388 | 185 |
| 19 | 150.9 | 424 | 196 |
| 24 | 157.8 | 444 | 203 |
| 29 | 157.2 | 442 | 210 |
| 34 | 152.0 | 427 | 216 |
| 39 | 145.4 | 409 | 222 |
| 44.5 | 139.4 | 392 | 227 |
| 47.5 | 136.4 | 384 | 229 |
| 52.5 | 133.9 | 377 | 230 |
| 57.5 | 130.8 | 368 | 231 |
| 61.5 | 111.6 | 314 | 231 |
| 66.5 | 86.8 | 244 | 230 |

A third series of results was obtained on the same preparation, as shown in Table VII:

TABLE VII

| ELAPSED TIME Min. | SHEAR STRESS LB/100 $F^2$ | VISCOSITY (cP) | TEMP. °F. | PRESS (psig) |
|---|---|---|---|---|
| 0 | 77.4 | 0 | 81 | 259 |
| 1 | 144.5 | 406 | 90 | 259 |
| 11 | 174.5 | 491 | 136 | 261 |
| 21 | 214.8 | 604 | 155 | 263 |
| 31 | 213.6 | 601 | 168 | 264 |
| 24 | 201.5 | 567 | 177 | 265 |
| 29 | 197.2 | 554 | 179 | 266 |
| 58 | 196.7 | 553 | 180 | 266 |
| 68 | 198.7 | 559 | 179 | 267 |
| 86 | 200.5 | 563 | 179 | 268 |
| 109 | 200.8 | 564 | 180 | 269 |

These also were highly stable after a prolonged period. In Table VIII, a gellant was prepared by mixing two components—the first was 67% phosphate ester, 6% KOH, and 27% solvent; the second was 54.4% ferric sulfate, 20.9% triethanolamine, 18.7% ethylene glycol, 3% ammonium cumene sulfate (a surfactant) and 3% water. These two components were mixed into Diesel oil at a concentration of 2 components of 1%. The resulting gelled hydrocarbon was tested in the Fann (model 50), viscometer in a manner similar to the above. For the series reported in Table VIII, the pressure increased gradually from 259 to 267 psig.

TABLE VIII

| ELAPSED TIME Min. | SHEAR STRESS LB/100 F$^2$ | VISCOSITY (cP) | TEMP. °F. |
|---|---|---|---|
| 0 | 70.6 | 0 | 130 |
| 5 | 191.1 | 538 | 151 |
| 10 | 194.7 | 547 | 160 |
| 15 | 197.6 | 555 | 167 |
| 20 | 201.2 | 566 | 172 |
| 25 | 202.8 | 570 | 177 |
| 28 | 202.2 | 569 | 179 |
| 33 | 199.2 | 560 | 181 |
| 38 | 194.5 | 547 | 182 |
| 55 | 182.2 | 512 | 181 |
| 100 | 173.4 | 488 | 179 |

The same compositions used for Table VIII were run again for the results in Table IX. In this case, the pressure was maintained at 244–245 psig.

TABLE IX

| ELAPSED TIME Min. | SHEAR STRESS LB/100 F$^2$ | VISCOSITY (cP) | TEMP. °F. |
|---|---|---|---|
| 0 | 74.2 | 0 | 105 |
| 1 | 172.0 | 484 | 129 |
| 5 | 159.8 | 449 | 183 |
| 9 | 124.9 | 351 | 218 |
| 16 | 92.6 | 260 | 255 |
| 24 | 78.2 | 220 | 277 |
| 32 | 74.8 | 210 | 290 |
| 38 | 73.9 | 208 | 298 |
| 46 | 73.9 | 208 | 300 |
| 52 | 73.9 | 208 | 300 |
| 56 | 73.9 | 208 | 300 |
| 82 | 73.8 | 208 | 299 |
| 112 | 73.8 | 208 | 299 |

The same compositions used for Tables VIII and IX were used for Table X. In Table X, the pressure dropped gradually from 240 psig to 237 psig. As in all Tables V–IX, the shear rate was maintained at 100±0.1.

TABLE X

| ELAPSED TIME Min. | SHEAR STRESS LB/100 F$^2$ | VISCOSITY (cP) | TEMP. °F. |
|---|---|---|---|
| 0 | 72.3 | 0 | 103 |
| 4 | 179.0 | 503 | 143 |
| 8 | 172.0 | 484 | 164 |
| 12 | 162.3 | 456 | 179 |
| 16 | 149.2 | 420 | 190 |
| 20 | 136.4 | 384 | 198 |
| 24 | 124.2 | 349 | 206 |
| 28 | 114.7 | 322 | 212 |
| 32 | 105.2 | 296 | 218 |
| 36 | 102.0 | 287 | 219 |
| 40 | 96.4 | 271 | 223 |
| 44 | 92.6 | 260 | 228 |
| 48 | 91.3 | 257 | 231 |
| 52 | 90.0 | 253 | 233 |
| 56 | 90.1 | 253 | 233 |
| 60 | 89.8 | 252 | 233 |
| 77 | 92.8 | 261 | 233 |
| 92 | 94.8 | 267 | 229 |
| 107 | 96.3 | 271 | 229 |
| 122 | 98.0 | 276 | 229 |

Excellent gels have also been made using the techniques recited below:

In this procedure, 55 g ferric sulfate was blended with 11 g monoisopropyl amine

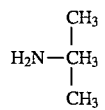

for a period of about an hour, then blended into Diesel oil containing a previously prepared mixture consisting of 67% phosphate ester, 15% KOH, and 18% solvent. The ferric sulfate-containing blend and the phosphate ester blend each comprised about 0.5 percent of the final fracturing fluid. The fracturing fluid was found to make a good gel overnight. A similar experiment substituting monobutyl amine provided an excellent gel overnight.

We claim:

1. Composition for fracturing formations comprising a hydrocarbon fracturing fluid and (a) about 0.3% to about 1.5% by weight of a phosphate ester of the formula HPO$_4$RR', where R is an alkyl, aryl, alkoxy, or alkaryl group having from 6 to about 18 carbon atoms and R' is hydrogen or an aryl, alkaryl, alkoxy, or alkyl group having from 1 to about 18 carbon atoms, (b) a ferric salt in an amount sufficient to form a gel with said hydrocarbon fluid and said phosphate ester, (c) a low molecular weight amine of the formula H$_{3-n}$N(C$_m$H$_{2m}$R)$_n$ where n is an integer from 1 to 3, each m is independently an integer from 2–6, and R is H or OH in an amount from about one-fourth molar equivalent to about one and one-half molar equivalent of the phosphate ester, and (d) up to about 10% surfactant.

2. Composition of claim 1 including a minor amount of KOH.

3. Composition of claim 1 wherein said low molecular weight amine has the formula N(CH$_2$CH$_2$R)$_3$ where R is H or OH.

4. Composition of claim 1 wherein said low molecular weight amine is present in an amount from one-half molar equivalent to one molar equivalent of the phosphate ester.

5. Composition of claim 1 wherein said low molecular weight amine is triethanolamine.

6. Method of claim 1 wherein said low molecular weight amine is triethylamine.

7. Composition of claim 1 wherein said ferric salt is present in an amount providing from 0.1 to 1.5 mole of ferric iron for each mole of phosphate ester.

8. Composition of claim 7 where in said ferric salt is present in an amount providing from about 0.8 to 1.2 mole of ferric iron for each mole of phosphate ester.

9. Composition of claim 1 wherein said ferric salt is ferric sulfate.

10. Composition of claim 1 wherein said surfactant is present in an amount from about 0.1% to about 10% of said composition.

11. Method of making a viscous hydrocarbon fracturing fluid comprising blending (a) a mixture of a phosphate ester, potassium hydroxide and a solvent with (b) a co-reacted mixture of an iron salt and a low molecular weight amine, in a hydrocarbon fracturing fluid.

12. Method of claim 11 wherein said phosphate ester is within the general formula $HPO_4RR'$ where R is a straight or branched chain alkyl, aryl, alkoxy, or alkaryl group having about 6 to about 18 carbon atoms and R' is hydrogen or an aryl, alkaryl, alkoxy, or alkyl group having up to about 18 carbon atoms.

13. Method of claim 11 wherein said iron salt is ferric sulfate.

14. Method of claim 11 wherein said low molecular weight amine is triethanolamine.

15. Method of claim 11 wherein the molar ratio of iron to phosphate is 0.25:1 to 1.5:1.

16. Method of claim 11 wherein the molar ratio of ferric salt to amine is 0.1:1 to 1.5:1.

\* \* \* \* \*